United States Patent [19]
Na et al.

[11] Patent Number: 5,336,507
[45] Date of Patent: Aug. 9, 1994

[54] USE OF CHARGED PHOSPHOLIPIDS TO REDUCE NANOPARTICLE AGGREGATION

[75] Inventors: George C. Na, Fort Washington; Natarajan Rajagopalan, Phoenixville, both of Pa.

[73] Assignee: Sterling Winthrop Inc., New York, N.Y.

[21] Appl. No.: 989,281

[22] Filed: Dec. 11, 1992

[51] Int. Cl.$^5$ .............................................. A61K 9/14
[52] U.S. Cl. ..................................... 424/489; 424/4; 424/484; 424/493; 424/497; 514/568
[58] Field of Search ............... 424/450, 4, 484, 489, 424/490, 491, 492–502; 436/829; 514/557, 568

[56]  References Cited

U.S. PATENT DOCUMENTS

| | | | |
|---|---|---|---|
| 4,894,234 | 1/1990 | Sharma et al. | 424/502 |
| 4,904,479 | 2/1990 | Illum | 424/490 |
| 5,091,188 | 2/1992 | Haynes | 424/450 |
| 5,145,684 | 9/1992 | Liversidge et al. | 424/499 |
| 5,151,264 | 9/1992 | Samain et al. | 424/502 |
| 5,188,837 | 2/1993 | Domb | 424/417 |
| 5,396,630 | 8/1983 | Riedl et al. | 424/502 |

FOREIGN PATENT DOCUMENTS 0498482  8/1992  European Pat. Off. .

*Primary Examiner*—G. S. Kishore
*Attorney, Agent, or Firm*—William J. Davis; Liza D. Hohenschutz

[57] ABSTRACT

This invention discloses a composition comprised of nanoparticles having a non-ionic surfactant as a surface modifier adsorbed on the surface thereof and a charged phospholipid as a cloud point modifier associated therewith, which cloud point modifier is present in an amount sufficient to increase the cloud point of the surface modifier. A preferred non-ionic surfactant surface modifier is a poloxamine or tyloxapol, and preferred charged phospholipid cloud point modifiers include dimyristoyl phosphatidyl glycerol. This invention further discloses a method of making nanoparticles having a non-ionic surfactant as a surface modifier adsorbed on the surface and a charged phospholipid as a cloud point modifier associated therewith, comprised of contacting said nanoparticles with the cloud point modifier for a time and under conditions sufficient to increase the cloud point of the surface modifier.

13 Claims, 1 Drawing Sheet

USE OF CHARGED PHOSPHOLIPIDS TO REDUCE NANOPARTICLE AGGREGATION

FIELD OF THE INVENTION

This invention relates to therapeutic and diagnostic compositions with a modified cloud point, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have a mean particle size of less than about 400 nanometers (nm).

As a result of their small size, sterilization of therapeutic and diagnostic agents in nanoparticulate form stabilized by a surface modifier (surfactant) is difficult. Filtration using a filter of 0.22 μm mesh size is sufficient to remove most bacteria and viruses, but the nanoparticles, due to their sizes, cannot be sterile filtered. Conventional autoclaving (steam heat) at 121° C. will result in substantial aggregation and/or growth of particle size, rendering the resulting particles unusable.

The aggregation of nanoparticles upon heating is directly related to the precipitation of the surface modifier (surfactant) at temperatures above the cloud point of the surfactant where the bound surfactant molecules are likely to dissociate from the nanoparticles and precipitate, leaving the nanoparticles unprotected. The unprotected nanoparticles can then aggregate into clusters of particles. Upon cooling, the surfactant redissolves into the solution, which then coats the aggregated particles and prevent them from dissociating into smaller ones. See FIG. 1.

This invention is directed to novel compositions that allow autoclaving of nanoparticles with reduced or no particle size growth. These compositions provide for a modification of the cloud point of the surface modifier in the composition such that the nanoparticles do not agglomerate during autoclaving. This invention is also directed to a method of making such compositions.

BRIEF SUMMARY OF THE INVENTION

Figure 1:
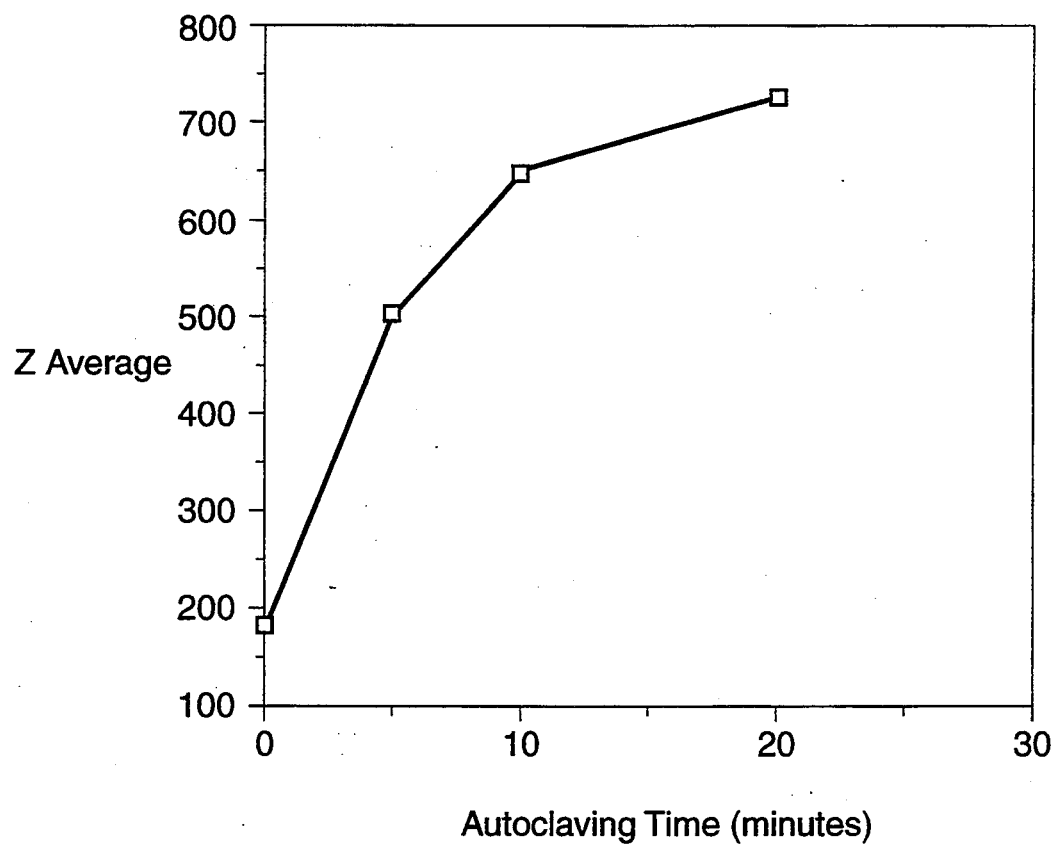
FIG. 1 is a plot of average versus autoclaving time illustrating particle size growth during heat sterilization.

This invention is directed to a composition comprised of nanoparticles having a non-ionic surfactant as a surface modifier adsorbed on the surface thereof and a charged phospholipid as a cloud point modifier associated therewith, which cloud point modifier is present in an amount sufficient to increase the cloud point of the surface modifier.

This invention is further directed to a method of making nanoparticles having a non-ionic surfactant as a surface modifier adsorbed on the surface thereof and a charged phospholipid as a cloud point modifier associated therewith, said method comprising contacting said nanoparticles with the cloud point modifier for a time and under conditions sufficient to increase the cloud point of the non-ionic surfactant.

DETAILED DESCRIPTION OF THE INVENTION

This invention is directed to a composition comprised of nanoparticles having a non-ionic surfactant as a surface modifier adsorbed on the surface thereof and a phospholipid as a cloud point modifier associated therewith, which cloud point modifier is present in an amount sufficient to increase the cloud point of the surface modifier. In a preferred embodiment, the cloud point of the non-ionic surfactant is increased above the temperature for autoclaving of the nanoparticles to prevent agglomeration.

The nanoparticles useful in the practice of this invention include a non-ionic surface modifier. Surface modifiers useful herein physically adhere to the surface of the therapeutic or diagnostic agent but do not chemically react with the agent or itself. Individually adsorbed molecules of the surface modifier are essentially free of intermolecular crosslinkages. Preferred surface modifiers can be selected from known non-ionic surfactants, including the poloxamines such as Tetronic TM 908 (also known as Poloxamine 908), which is a tetrafunctional block copolymer derived from sequential addition of propylene oxide and ethylene oxide to ethylenediamine, available from BASF, or Tetronic 1508 (T-1508), or a polymer of the alkyl aryl polyether alcohol type, such as tyloxapol.

The surface modifiers are commercially available and/or can be prepared by techniques known in the art. Two or more surface modifiers can be used in combination.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684, and EP-A 498,482. A preferred diagnostic agent is the x-ray imaging agent WIN-8883 (ethyl 3,5-diacetoamido-2,4,6-triiodobenzoate), the ethyl ester of diatrazoic acid.

As used herein, particle size refers to a mean particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a particle size of less than about 400 nm when measured by the above-noted techniques. In preferred embodiments of the invention, the effective average particle size is less than about 300 nm, and more preferably less than about 250 nm. In some embodiments of the invention, an effective mean particle size of less than about 200 nm has been achieved. With reference to the effective mean particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

As noted elsewhere herein, sterile filtration will not provide adequate sterilization for nanoparticles. Therefore, other methods of sterilization are required. For example, steam or moist heat sterilization at temperatures of about 121° C. for a time period of about 15 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

Sterilization takes place in the presence of cloud point modifiers such as charged phospholipids.

The cloud point is the temperature at which the surface modifier (surfactant) precipitates out of solution as described above. By the phrase "cloud point modifier" is meant a compound which influences the cloud point of surface modifiers. In particular, the cloud point modifiers useful in the present invention raise the cloud point of the surface modifiers in the compositions. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

Examples of cloud point modifiers include charged phospholipids. Charged phospholipids include any lipid having a net charge, i.e., any ionic phospholipid with a net positive or negative charge. Examples include such phospholipids as the synthetic phospholipid dimyristoyl phosphatidyl glycerol (DMPG), 1-palmitoyl-2-oleoyl phosphatidyl-serine, DL-alpha-phosphatidyl-L-serine-dipalmitoyl, and cardiolipin (diphosphatidyl glycerol). Synthetic phospholipids are typically available in high purity and are relatively stable and physiologically tolerable. A preferred phospholipid is a negatively charged phospholipid. A preferred negatively charged phospholipid is dimyristoyl phosphatidyl glycerol.

The charged phospholipid can be present in an amount of 0.005–20%, preferably 0.01–15%, more preferably 0.05–10%, by weight based on the total weight of the nanoparticle suspension.

Isotonicity refers to the osmotic pressure of a solution. A solution which will be administered into the blood stream of an individual is typically prepared such that the osmotic pressure of that solution is the same as the osmotic pressure of blood. Such a solution is said to be isotonic.

An isotonicity maintaining compound is a compound which provides for the maintenance or alteration of a solution so as to make that solution isotonic. Such an isotonicity maintaining compound will adjust the osmotic pressure of a solution containing the compositions of the present invention so as to provide, or maintain, an isotonic solution.

Exemplary isotonicity maintaining compounds include mannitol, dextrose, sodium chloride, potassium chloride, and Ringer's lactate. Preferred isotonicity maintaining compounds include mannitol and dextrose.

The pH value of a solution to be delivered into the body of a subject is also an important factor. Typically, pH values should not be either too acidic or too basic. To maintain the appropriate pH value of a solution, it is preferable to provide pH value maintaining compounds. These compounds provide a buffering capacity to the solution, to prevent extremes of pH values of the solution upon storage or upon subsequent manipulation.

Exemplary pH value maintaining compounds include the well known buffers such as Tris base, HEPES, carbonate, phosphate, citrate and acetate salts. A preferred buffer is sodium phosphate (either mono- or di-basic, or both).

The composition of the present invention can be further provided with a non-ionic surfactant after sterilization (such as by autoclaving). The purpose of this additional non-ionic surfactant is to help mask the charges on the surface of the nanoparticles containing phospholipids according to the present invention. Masking these charges imparts longer circulation time for the nanoparticles used in intravenous applications.

This invention further discloses a method of making nanoparticles having a non-ionic surface modifier adsorbed on the surface and a charged phospholipid cloud point modifier associated therewith, comprised of contacting said nanoparticles with the cloud point modifier for a time and under conditions sufficient to increase the cloud point of the surface modifier.

This method involves the preparation of therapeutic or diagnostic nanoparticles, as discussed elsewhere herein, and contacting those nanoparticles with a cloud point modifier. Contacting may be by admixing a suspension of nanoparticles with a solution of cloud point modifier, followed by sterilization at a temperature and for a time sufficient to effect sterilization of the nanoparticle suspension.

The following examples further illustrate the invention and are not to be construed as limiting of the specification and claims in any way.

Example 1. Effect of phospholipids on the particle size of WIN 8883/Tyloxapol nanoparticles.

Samples were prepared according to the following general protocol. 0.001 grams (g) each of the tested phospholipids was weighed into individual 2 ml vial. Then, 0.5 ml of WIN 8883/Tyloxapol nanoparticle suspension comprised of the diagnostic agent WIN 8883 (the ethyl ester of diatrazoic acid) plus the surfactant tyloxapol was then added to each vial. The samples were then sonicated for 15 minutes. Unless otherwise stated, each sample was next autoclaved at 121° C. for 20 minutes. After the samples were cooled, 10 μl of each sample was diluted to 15 ml in Malvern buffer and tested for particle size and zeta potential.

The following phospholipids were tested:
(a) POPS: 1-Palmitoyl-2-oleoyl-phosphatidylserine
(b) DPPS: Dilpalmitoylphosphatidylserine
(c) DPPE: Dipalmitoylphosphatidylmonomethylethanolamine
(d) DMPG: Dimyristoylphosphatidylglycerol
(e) Cardiolipin The data are presented in Table 1.

TABLE 1

| Effect of Phospholipids on the Nanoparticulate Suspension Upon Autoclaving | | |
|---|---|---|
| Additive | Mean Particle Size (nm) | Zeta Potential (mV) |
| Samples in the following study contained 15% WIN-8883 and 3% Tyloxapol | | |
| None (not autoclaved) | 159 | −6 |
| 0.35% Cardiolipin | 162 | −28 |
| 0.2% POPS | 164 | −22 |
| 0.5% POPS | 175 | −34 |
| 0.2% DPPS | 281 | −18 |
| 0.5% DPPS | 266 | −20 |
| 0.2% DPPE | 469 | −8 |
| None (not autoclaved) | 202 | −6 |
| 0.2% DMPG | 235 | −20 |
| 0.2% Cardiolipin | 326 | −15 |
| 0.2% DPPS | 309 | −14 |
| Samples in the following study contained | | |

TABLE 1-continued

Effect of Phospholipids on the Nanoparticulate Suspension Upon Autoclaving

| Additive | Mean Particle Size (nm) | Zeta Potential (mV) |
|---|---|---|
| 15% WIN 8883 and 3.5% Tetronic 908. | | |
| None (not autoclaved) | 173 | −0.9 |
| 0.2% Cardiolipin | 367 | −4 |
| 0.5% DMPG | 490 | −26 |

Example 2. Effect of phospholipids on the particle size of WIN 8883 nanoparticles with other surface modifiers.

The procedure described in Example 1 was used to examine the effects of the phospholipid DMPG on nanoparticles prepared with surfactants such as T908, DM970 (Rhône-Poulenc), RE960 (Rhône-Poulenc) and CO990 (Rhône-Poulenc). DM970 and CO990 are alkyl phenol ethoxylates. RE960 is an anionic surfactant, i.e., polyethoxylated nonylphenol phosphate. The results of these experiments are shown in Tables 2 and 3.

TABLE 2

All samples contain 15% WIN 8883, 0.2% DMPG and 3% of a surfactant specified in the first column.

| Surfactant | Mean Particle Size (nm) | Zeta Potential (mV) | Polydispersity |
|---|---|---|---|
| Before Autoclaving at 121° C./20 min | | | |
| None | 201 | | 0.16 |
| T-908 | 174 | | 0.13 |
| Autoclaved at 121° C./20 min | | | |
| None | 284 | −58 | 0.20 |
| T-908 | 502 | −39 | 0.22 |
| DM970 | 731 | −33 | 0.31 |
| CO990 | 654 | −48 | 0.29 |
| Before Autoclaving at 121° C./20 min | | | |
| None | 238 | −52 | 0.17 |
| T-908 | 192 | −12 | 0.15 |
| DM970 | 191 | −16 | 0.16 |
| CO990 | 190 | −38 | 0.17 |
| Added 0.25% extra DMPG and Autoclaved at 121° C./20 min (Total 0.45% DMPG) | | | |
| None | 234 | −60 | 0.13 |
| T-908 | 477 | −37 | 0.246 |
| DM970 | 583 | −37 | 0.295 |
| CO990 | 628 | −48 | 0.248 |

TABLE 3

All samples contained 15% WIN 8883

| Excipients | Autoclave Sterilization (121° C./20 min) | Mean Size (nm) | Polydispersity |
|---|---|---|---|
| 0.2% DMPG | no | 196 | 0.14 |
| 0.2% DOSS | no | 205 | 0.15 |
| 3% DM970, 10% PEG-400 | no | 183 | 0.21 |
| 3% DM970, 0.2% DMPG | no | 193 | 0.18 |
| 0.2% DMPG | yes | 709 | 0.24 |
| 0.5% DMPG | yes | 279 | 0.26 |
| 0.2% DOSS | yes | 640 | 0.27 |
| 0.5% DOSS | yes | 278 | 0.24 |
| 10% PEG-400 | yes | 592 | 0.30 |
| 0.2% RE960 | yes | 747 | 0.29 |

EXAMPLE 3. Effect of various phospholipids on particle size distribution.

The procedure described in Example 1 was used to examine the effects of various phospholipids on nanoparticles. The results of these experiments are shown in Tables 4 and 5.

TABLE 4

All samples contained 15% WIN 8883. Unless otherwise stated, all samples were autoclaved at 121° C. for 20 minutes.

| [DMPG] | Mean Particle Size (nm) | Polydispersity |
|---|---|---|
| 0.2% (not autoclaved) | 196 | 0.174 |
| 0.2% | 242 | 0.134 |
| 0.2% | 224 | 0.194 |
| 0.4% | 239 | 0.199 |
| 0.7% | 239 | 0.187 |
| 1.2% | 251 | 0.193 |

TABLE 5

| Phospholipid | Autoclave (121° C./20 min) | Mean Size (nm) | Polydispersity |
|---|---|---|---|
| None | no | 159 | 0.143 |
| 0.5% POPS | yes | 174 | 0.157 |
| 0.2% POPS | yes | 164 | 0.137 |
| 0.5% DPPS | yes | 266 | 0.137 |
| 0.2% DPPS | yes | 281 | 0.141 |
| 0.2% DPPE | yes | 469 | 0.135 |
| 0.35% Cardiolipin | yes | 162 | 0.141 |

Example 4. Effects of various phospholipids on the cloud point of tyloxapol.

Most phospholipids with negative charge raise the cloud point of tyloxapol and stabilize the particle size after 121° C. for 20 minutes. Lipids were weighed directly into a 2 ml vial which 1 ml filled and bath sonicated to dissolve. The cloud point of 1% tyloxapol with various lipids is shown in Table 6.

TABLE 6

| Phospholipid | Cloud Point (°C.) |
|---|---|
| none | 96 |
| 0.1% POPS | >130 |
| 0.5% POPS | >130 |
| 0.1% DPPS | 117 |
| 0.1% DPPE | 96 |
| 0.5% Cardiolipin | 120 |
| 0.1% Cardiolipin | >130 |

The foregoing specification, including the specific embodiments and examples is intended to be illustrative of the present invention and is not to be taken as limiting. Numerous other variations and modifications can be effected without departing from the true spirit and scope of the present invention.

We claim:

1. A composition comprised of nanoparticles comprised of a therapeutic or diagnostic agent having 0.1 to 90% by weight of said nanoparticles of a non-ionic surfactant as a surface modifier adsorbed on the surface of said therapeutic or diagnostic agent, said nanoparticles having from 0.005 to 20% by weight of said composition of a charged phospholipid as a cloud point modifier on the surface of said nanoparticles.

2. The composition of claim 1 wherein said diagnostic agent is the ethyl ester of diatrazoic acid.

3. The composition of claim 1 wherein said non-ionic surfactant is selected from the group consisting of a poloxamine and an alkyl aryl polyether alcohol polymer.

4. The composition of claim 3 wherein said poloxamine is a tetrafunctional block copolymer derived from sequential addition of propylene oxide and ethylene oxide to ethylenediamine.

5. The composition of claim 3 wherein said alkyl aryl polyether alcohol polymer is tyloxapol.

6. The composition of claim 1 wherein said phospholipid is diacylphosphatidyl glycerol.

7. The composition of claim 1 wherein said phospholipid is dimristoyl phosphatidyl glycerol.

8. The composition of claim 1 further comprising an isotonicity maintaining compound.

9. The composition of claim 8 wherein said isotonicity maintaining compound is selected from the group consisting of mannitol or dextrose.

10. The composition of claim 1 further comprising a pH value maintaining compound.

11. The composition of claim 10 wherein said pH value maintaining compound is sodium phosphate.

12. The composition of claim 1 further comprising a non-ionic surfactant added after sterilization of said composition.

13. The composition of claim 10 wherein said non-ionic surfactant is a poloxamine.

* * * * *